US007445600B1

(12) United States Patent
Carr et al.

(10) Patent No.: US 7,445,600 B1
(45) Date of Patent: Nov. 4, 2008

(54) MULTI-FUNCTION, SELF-SERVICE HEALTH KIOSK

(75) Inventors: Arthur G. Carr, Washington, DC (US); Samuel G. Guss, Frederick, MD (US); Thomas E. Piston, Jr., Boonsboro, MD (US); Robert D. Rosenthal, Silver Spring, MD (US)

(73) Assignee: Futrex, Inc., Gaithersburg, MD (US)

( * ) Notice: Subject to any disclaimer, the term of this patent is extended or adjusted under 35 U.S.C. 154(b) by 284 days.

(21) Appl. No.: 11/067,723

(22) Filed: Mar. 1, 2005

Related U.S. Application Data

(60) Provisional application No. 60/548,168, filed on Mar. 1, 2004.

(51) Int. Cl.
*A61B 5/00* (2006.01)
*A61B 6/00* (2006.01)

(52) U.S. Cl. .................. 600/490; 600/300; 600/473; 600/485

(58) Field of Classification Search .......... 600/300, 600/301, 309, 310, 481, 485, 490, 492
See application file for complete search history.

(56) References Cited

U.S. PATENT DOCUMENTS

| | | | |
|---|---|---|---|
| 3,935,984 A * | 2/1976 | Lichowsky et al. | 600/499 |
| 4,633,087 A | 12/1986 | Rosenthal et al. | |
| 4,798,955 A | 1/1989 | Rosenthal | |
| 4,850,365 A | 7/1989 | Rosenthal | |
| 4,928,014 A * | 5/1990 | Rosenthal | 250/341.5 |
| 4,990,772 A | 2/1991 | Rosenthal | |
| 5,028,787 A | 7/1991 | Rosenthal et al. | |
| D320,662 S | 10/1991 | Nakai | |
| 5,086,229 A | 2/1992 | Rosenthal et al. | |
| 5,134,302 A | 7/1992 | Rosenthal | |
| 5,218,207 A | 6/1993 | Rosenthal | |
| 5,324,979 A | 6/1994 | Rosenthal | |
| 5,365,066 A | 11/1994 | Krueger, Jr. et al. | |
| 5,413,582 A * | 5/1995 | Eaton | 606/202 |
| 6,066,847 A | 5/2000 | Rosenthal | |
| 6,134,458 A * | 10/2000 | Rosenthal | 600/310 |
| 6,205,354 B1 | 3/2001 | Gellermann et al. | |
| 6,336,044 B1 * | 1/2002 | Ghiassi et al. | 600/473 |
| 6,400,972 B1 | 6/2002 | Fine | |
| 6,477,392 B1 | 11/2002 | Honigs et al. | |
| 6,587,704 B1 | 7/2003 | Fine et al. | |
| 6,748,264 B2 * | 6/2004 | Chai | 600/546 |

OTHER PUBLICATIONS

Ermakov, I.V., et al., "Resonance Raman Detection of Carotenoid Antioxidants in Living Human Tissues", Optics Letters, Aug. 1, 2001, vol. 26, No. 15, pp. 1179-1181.

* cited by examiner

*Primary Examiner*—Robert L Nasser
(74) *Attorney, Agent, or Firm*—Rothwell, Figg, Ernst & Manbeck

(57) ABSTRACT

In one aspect, the present invention provides a multi-function, self-service health kiosk. In another aspect, the present invention provides a wheelchair accessible health kiosk. In another aspect, the present invention provides a blood pressure measurement apparatus for use in a health kiosk.

14 Claims, 16 Drawing Sheets

MULTI-FUNCTION, SELF-SERVICE HEALTH KIOSK

The present invention claims the benefit of U.S. Provisional Patent Application No. 60/548,168, filed on Mar. 1, 2004, the content of which is incorporated herein by this reference.

BACKGROUND OF THE INVENTION

1. Field of the Invention

The present invention relates to the field of health kiosks.

2. Discussion of the Background

Automated self-testing blood pressure and heart rate kiosks have been available for many years in many retail stores and pharmacies. These kiosks have proved to be popular with the public to provide health information. U.S. Pat. No. 6,336,044, the content of which is incorporated herein by this reference, discloses adding a percent body fat measuring system, which uses near-infrared technology, to kiosks that measure blood pressure and heart rate.

The body fat measurement technology disclosed in U.S. Pat. No. 6,336,044 requires generating multiple wavelengths. This requirement causes the measurement system to be somewhat costly and relatively large, thereby compromising the blood pressure measurement.

Another disadvantage of conventional self-service health kiosks is that they cannot accommodate a large range of arms sizes and/or are mechanically complex and difficult to maintain. Blood pressure measurements in self-service kiosks have been implemented using two different approaches. The first approach uses a fixed diameter circular tube with an internal cuff that is attached to the tube's inside surface. The cuff contains an inflatable bladder. After the arm is inserted into the cuff, the bladder is inflated until the cuff comes in contact with the arm and is then further inflated to a pressure suitable for starting the blood pressure measurement.

This "rigid tube approach" has two distinct disadvantages. First, the maximum diameter arm is limited by the internal diameter of the rigid tube. Second, when a person with a very small diameter arms insert their arm in the tube, the bladder must be "hyper-inflated" (i.e., the bladder must be inflated to such an extent that it is difficult for an accurate measurement to be achieved). This limits the inner diameter of the rigid tube to about 5 inches, thereby not allowing measurement of people with large diameter arms.

The second approach to blood pressure measurements is typified by U.S. Pat. No. 6,336,044. In the second approach, after the arm is inserted an automated mechanism mechanically tightens the cuff around the arm prior to inflation. This is analogous to what a doctor does during normal blood pressure measurement.

These mechanized approaches also suffer from disadvantages. First, they are mechanically complex and difficult to keep in working order in non-attended kiosks. Second, the "wrapping mechanism" approach makes it difficult to remove the arm when the mechanism is in the wrapped position. This raises concerns because, in an emergency situation where power may be interrupted or a fire occurs in the facility and the person panics, the person using the kiosk may not be able to extract him or herself from the wrapping mechanism.

In addition to the above disadvantages of conventional blood pressure measurement kiosks, such kiosks do not provide meaningful measurements of other health related parameters. Another problem with the most conventional blood pressure measurement kiosks is such kiosks are not designed for use by people in wheel chairs.

In some designs, there is wheelchair accessibility, but all such designs have severe limitations. For example, one design uses a bench seat that is built into a rail in the back wall of the kiosk. The bench seat then needs to be moved totally forward to allow a wheelchair to enter. Such an approach has the limitation of being too prone to vandalism from kids putting gum or other debris into the sliding channel.

What is desired is a health kiosk that overcomes these and/or other disadvantages of conventional health kiosks.

SUMMARY OF THE INVENTION

In one aspect, the present invention provides an improved body fat measurement apparatus that is smaller and/or less costly than the conventional body fat measurement systems described above. Advantageously, the improved body fat measurement apparatus may be a component of a self-service health kiosk.

In one embodiment, the body fat measurement apparatus includes a first infrared emitting diode (IRED), a IRED spaced apart from the first IRED and a sensor disposed midway or about midway between the diodes. Preferably each IRED is configured to emit a single wavelength of light. In one embodiment, the wave length is about 940 nanometers. In some embodiments, the body fat measurement apparatus also includes a heater circuit. In some embodiments, the heater circuit, IREDs and sensor are all housed in a single housing.

In another aspect, the present invention provides an improved blood pressure measurement apparatus. The improved apparatus aims to eliminate the loss in potential accuracy due to "hyper-inflation" of a bladder, accommodate a larger range of arm sizes, and eliminate an arm being restrained during an emergency situation, such as a power outage or other emergency situation. Advantageously, the improved blood pressure measurement apparatus may be a component of a self-service health kiosk.

In some embodiments, the blood pressure measurement apparatus includes: a tubular or semi-tubular support member having an inner surface and an outer surface; a roller; and a cuff having a first end and a tail portion, the first end being fixed to the inner surface of the support member and the tail portion passing through a slit in the support member and being at least partially wound around the roller, wherein the cuff includes a casing housing an inflatable bladder and a generally hard yet flexible and resilient frame. In preferred embodiments, the frame is or includes a generally solid rectangular hard yet flexible member, which member may be constructed out of plastic or other sturdy, flexible material or any combinations of such.

In another aspect, the present invention provides a health kiosk that includes a fingertip light transmission sensor. The fingertip light transmission sensor (or "finger clip sensor") may be used to non-invasively provide to a user: (1) a measurement corresponding to the user's blood circulation, (2) a measurement corresponding to percent oxygen saturation in the user's blood, and/or (3) a measurement of various blood analytes including blood glucose and cholesterol concentration.

In another aspect, the present invention provides a health kiosk that provides wheelchair access. In some embodiments, the wheelchair accessible health kiosk, includes: a first support placed on a generally flat surface; a seat placed on the generally flat surface and connected to the first support; and a blood pressure measurement apparatus attached to a second support, wherein the second support is pivotally connected to the first support such that the second support and the blood pressure measurement apparatus, which is fixed to the second support, may rotate generally about an axis that is perpendicular to the generally flat surface, and thereby move away from the first support.

In other embodiments, the wheelchair accessible health kiosk includes: a leg comprising a first end section, a second end section and an interim section between the first end section and the second end section, wherein the first end section is configured to be placed on a floor; a rigid support pivotally attached to the second end section so that the support is rotatable about an axis that is generally perpendicular with the floor; and a blood pressure measurement apparatus fixed to the rigid support so that the blood pressure measurement apparatus rotates with the rigid support.

The above and other aspects, features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, help illustrate various embodiments of the present invention and, together with the description, further serve to explain the principles of the invention and to enable a person skilled in the pertinent art to make and use embodiments of the invention. In the drawings, like reference numbers indicate identical or functionally similar elements.

DETAILED DESCRIPTION OF PREFERRED EMBODIMENTS

The following contains a description of various aspects of the invention. For convenience, these aspects have been subdivided under specific headings.

Blood Pressure Apparatus:

As previously described, the two current methods of performing blood pressure measurements in kiosks have major drawbacks. The most common method (using a fixed diameter tube that contains an inflatable cuff) is limited to arms smaller than the internal diameter of the tube with the blood pressure cuff installed. Additionally, arms of small diameter require the bladder to be hyper-inflated, and therefore, lose measurement sensitivity. The other approach that is used (using mechanical systems to wrap the cuff around the arm) introduces problems of mechanical complexity as well as difficulties in releasing the arm during an emergency condition. The blood pressure apparatus described below aims to overcome at least some, if not all, of these limitations.

Figure 1:
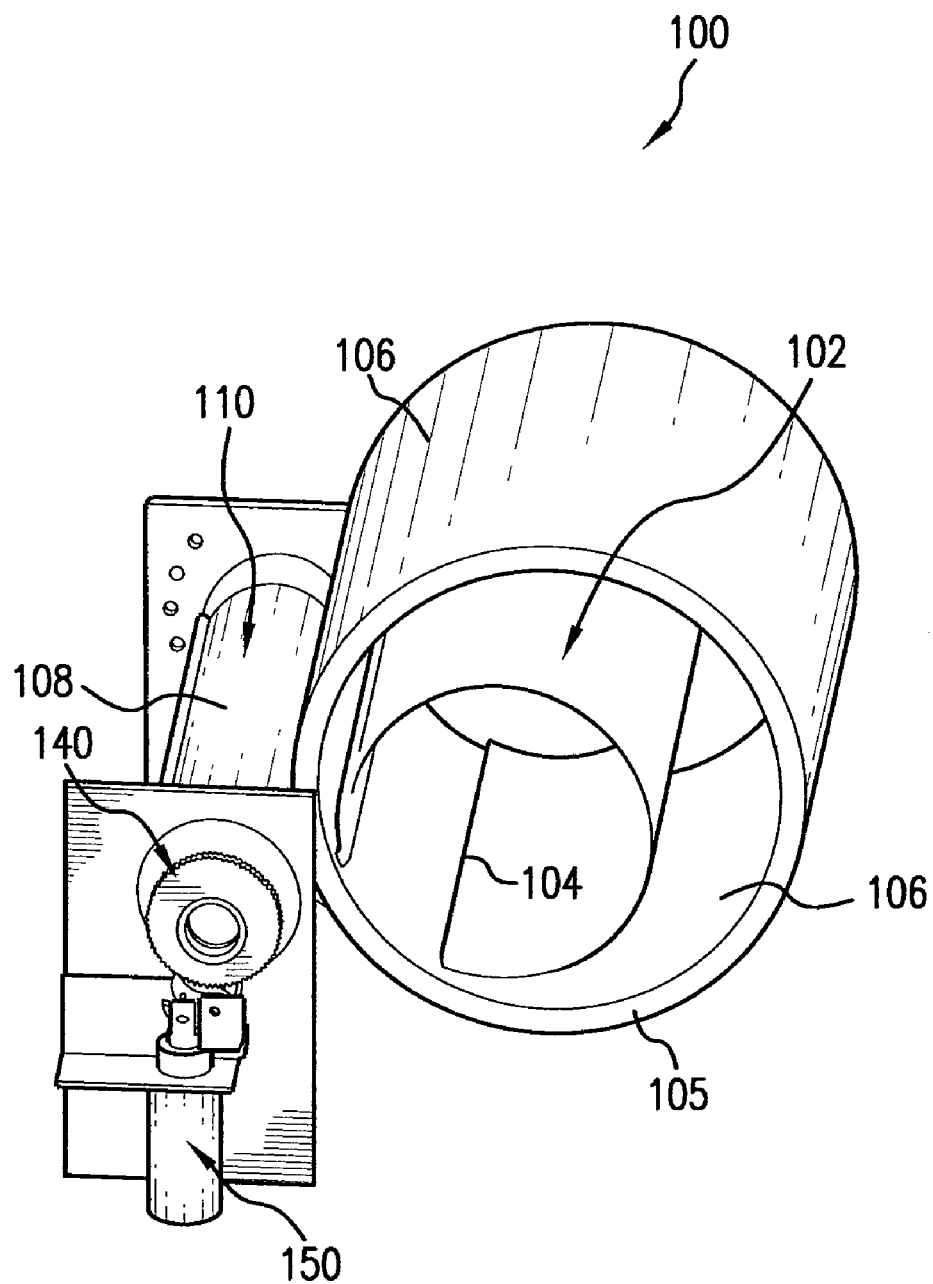
FIG. 1 is a schematic diagram of a blood pressure measurement apparatus according to an embodiment of the invention.

FIG. 1 illustrates a blood pressure measurement apparatus 100 according an embodiment of the invention. Apparatus 100 includes an inflatable cuff 102 having an end 104 fixed to a rigid support 106 and having a tail portion 108 that passes through a slit in support 106 and wraps around a roller 110.

As shown in FIG. 1, cuff 102 has a curved tubular shape when tail portion 108 is wrapped around roller 110 and end 104 is fixed to support 106. Preferably, as will be described with reference to FIGS. 3 and 4, cuff 102 includes an internal hard yet flexible, resilient frame that functions to enable cuff 102 to maintain its tubular shape.

Figure 2:
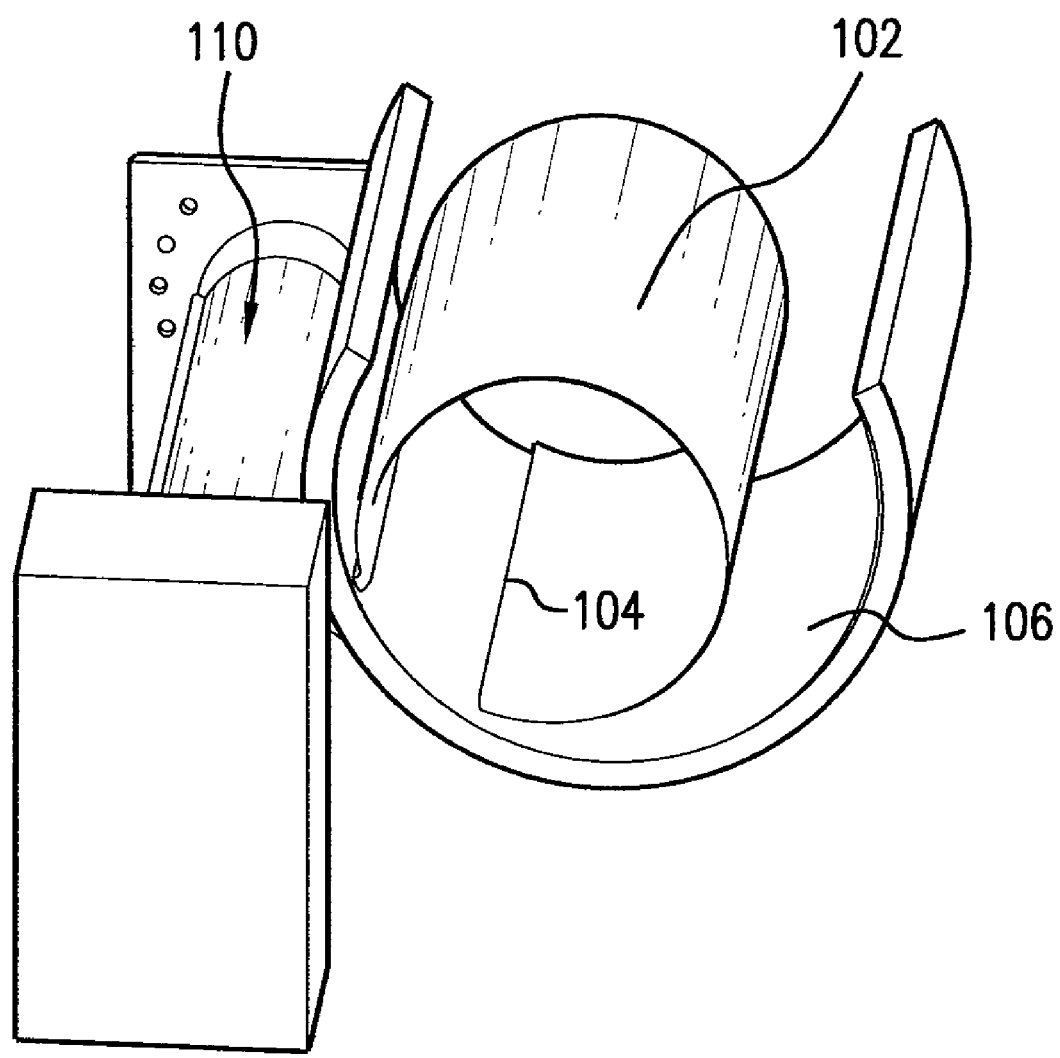
FIG. 2 is a schematic diagram of a blood pressure measurement apparatus according to another embodiment of the invention.

In the embodiment shown in FIG. 1, rigid support 106 is in the shape of a tube. In this embodiment, support 106 preferably has an internal diameter of about six inches. Such a diameter allows a rather large arm (e.g., an arm having a maximum circumference of sixteen inches) to be inserted into support 106. Conventional kiosk blood pressure units have a limitation of a fourteen inch arm circumference. An alternate to using a rigid external tube as support 106 is to use only part of a tube (e.g., omitting the top half) as support 106, as shown in FIG. 2. This approach has merit because it allows more freedom in entering the arm into cuff 102.

Figure 3:
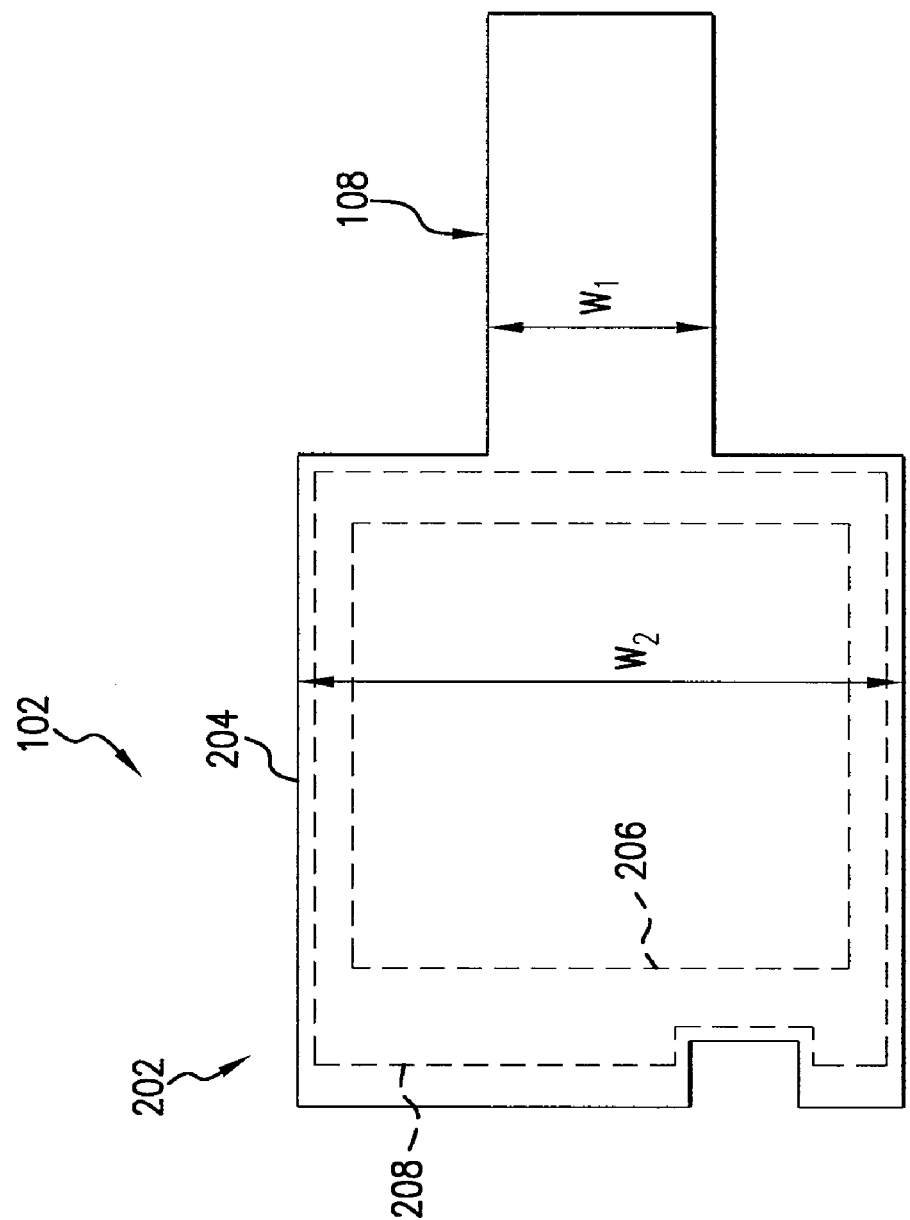
FIG. 3 is a top view of a blood pressure measurement cuff according to an embodiment.

Referring now to FIG. 3, FIG. 3 is a top view of cuff 102 according to an embodiment of the invention. As shown in FIG. 3, cuff 102 includes a tail portion 108, which is designed to wrap around roller 110 in the same way that a window shade wraps around a window-shade roller. Tail portion 108 is attached to a body portion 202. In the embodiment shown, the width (w1) of tail portion 108 is different than (e.g., less than) the width (w2) of the body portion 202, however, in other embodiments the widths may be same.

According to some embodiments, body portion 202 of cuff 102 includes a casing 204 that encases a bladder 206 and a hard, flexible internal frame 208. In preferred embodiments, the frame 208 is or includes a generally solid rectangular hard yet flexible member, which member may be constructed out of plastic or other sturdy, flexible material or any combinations of such. These features are illustrated in FIG. 4, which shows a cross-sectional side view of a portion of cuff 102.

Figure 4:
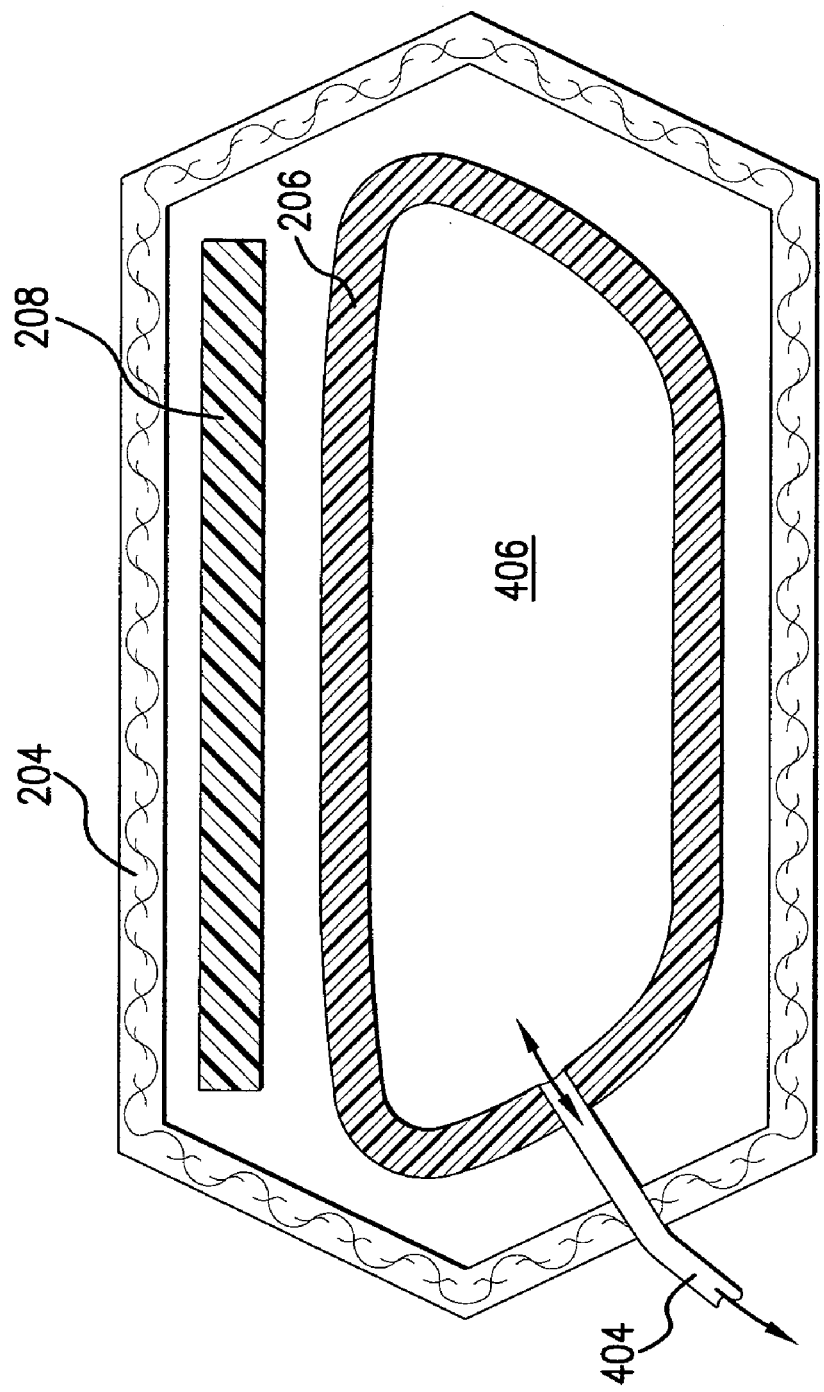
FIG. 4 is a cross-sectional, side view of the cuff shown in FIG. 3.

Referring now to FIG. 4, FIG. 4 illustrates that bladder 206 and frame 208 are housed within casing 204. Casing 204 may be made of a durable material such as Lycra and tail portion 108 may be made from a cloth material. Preferably, frame 208 is flexible (e.g., capable of being bent or flexed). Frame 208, in its neutral position, is generally planar. Preferably, frame 208 is resilient so that when it is bent it will return to its original planar shape. As further shown in FIG. 4, an air passage (e.g., a tube) 404 allows air to flow into and out of the cavity 406 defined by bladder 206.

Referring back to FIG. 1 and to roller 110, roller 110 preferably contains an internal torsion spring similar to that used in window shades. During non-use, roller 110's internal torsion spring provides a torque equal to and in the opposite direction than the torque provided by cuff 102's internal frame 208. If a large arm is inserted into cuff 102, the arm's insertion causes extra torque on roller 110 allowing additional tail portion 108 to be unwound from the roller 110. When the arm is removed, roller 110 returns to its neutral initial state, thereby winding tail portion around roller 110.

In some embodiments, rigidly attached to one end of roller 110 is a ratchet wheel 140, which may have radial curved teeth. Below ratchet wheel 140 is a solenoid 150 that operates a pawl (not shown). In a non-measurement mode, the pawl is not engaged with the ratchet wheel, thereby allowing the roller to rotate, but is rather held in an open position by a retraction spring.

After an arm is inserted into cuff 102 and a blood pressure measurement is initiated (e.g., a user activated the "START measurement" button) two alternate conditions can occur.

The first condition occurs when the subject's arm is smaller than the neutral diameter of cuff 102 (e.g., an arm circumference of less than eleven inches). In such a situation the subject's arm will fit within cuff 102 without tail portion 108 of cuff 102 needing to unwind off roller 110. After the START measurement button is pressed, solenoid 150 is powered and the pawl locks the ratchet wheel 140 so that roller 110 can not rotate (i.e., the cuff 102 cannot unroll). Additionally, bladder 106 starts to inflate and expands pressing the arm against a surface of support 106.

For the small arm situation, bladder 206 may not need to hyper-extend because the starting position of the cuff is, in some embodiments, less than the five inch diameter as in conventional kiosk blood pressure units. This allows the measurement to have good sensitivity even on very small arms (e.g., arms less than nine inches in circumference). Moreover, there is relatively little, if any, mechanical complexity with the straightforward solenoid lock system as described.

The second condition occurs when the subject's arm is larger in diameter than the inner-diameter of cuff 102 when cuff 102 is in its neutral position. In this situation, when the subject's arm is inserted into cuff 102, the motion of the arm being inserted provides an expanding force on cuff 102 that causes tail portion 108 of cuff 102 to start unrolling off roller 110. Because of the torsion spring in roller 110, which pulls on tail portion 108, cuff 102 only unrolls sufficiently for the exact arm diameter. When the START measurement button is pressed, solenoid 150 is activated causing the pawl to engage ratchet wheel 140, thereby locking roller 110 so that it can not rotate. The lock arrangement stays in force while the bladder 206 is inflated and the blood pressure measurement is being made.

Because of the ability to have the cuff unroll and be in contact with larger arms, the design is not limited to the conventional 13 or 14 inch circumference arms. With a design described according to an embodiment of the invention, the arm circumference that could be measured may be sixteen inches. This will allow approximately ninety-nine percent of the total U.S. adult population to be measured.

When the blood pressure measurement is completed, the power to solenoid 150 is preferably shut off. This allows the solenoid retraction spring to release the pawl from ratchet wheel 140 that is mounted onto roller 110, thereby freeing the roller to rotate. This insures that as the arm is removed, the roller returns cuff 102 to its neutral position.

In summary, this new method of performing blood pressure measurement has the distinct advantage over the previous methods in that it is simple, it allows a larger range of arm diameters to be measured, and it does not have the wrapping mechanism complexity.

Body Fat Measurement:

Various U.S. patents teach the use of near-infrared measurements, in combination with certain physical parameters, to determine the percent body fat in human beings. These patents can be considered in three different groups. The first group teaches using two wavelengths to provide a measurement (e.g., U.S. Pat. No. 4,850,365, the content of which is incorporated herein by this reference). In this approach, two wavelengths are combined with physical parameters such as height, weight, exercise level, etc., via Multiple Linear Regression equations for final determination of percent body fat.

The second group teaches using up to six different wavelengths for determining percent body fat (e.g., U.S. Pat. No. 6,134,458, the content of which is incorporated herein by this reference). This approach also uses physical parameters, however, the need for using an empirical parameter such as "degree of exercise level" is not needed.

The third group uses a single wavelength in combination with physical parameters such as height, weight, etc. (U.S. Pat. No. 4,928,014, the content of which is incorporated herein by this reference). In this approach, a small loss in accuracy is accepted in order to be able to produce a product that is much less costly.

A variation of the second of the above described approaches was used for kiosk measurement of near-infrared percent body fat (U.S. Pat. No. 6,336,044). This patent taught that the multi-wavelength approach (i.e., approach 2 described above) could also provide highly accurate percent body fat on measurements at a fixed distance from the elbow on the rear of the arm in the triceps region. This method of measuring body fat has been implemented successfully in kiosk design. However, as previously stated, it is expensive and has a relatively large size, that potentially interferes with the accuracy of the blood pressure measurement.

According to an embodiment of the invention, a body fat measurement apparatus is provided that uses the single wavelength approach and is designed to perform the measurements on the rear side of the arm at a fixed distance from the elbow in the region of the triceps. This measurement approach, when used with suitable physical parameters such as height, weight, gender and age, provides a highly accurate measurement of percent body fat.

Figure 5:
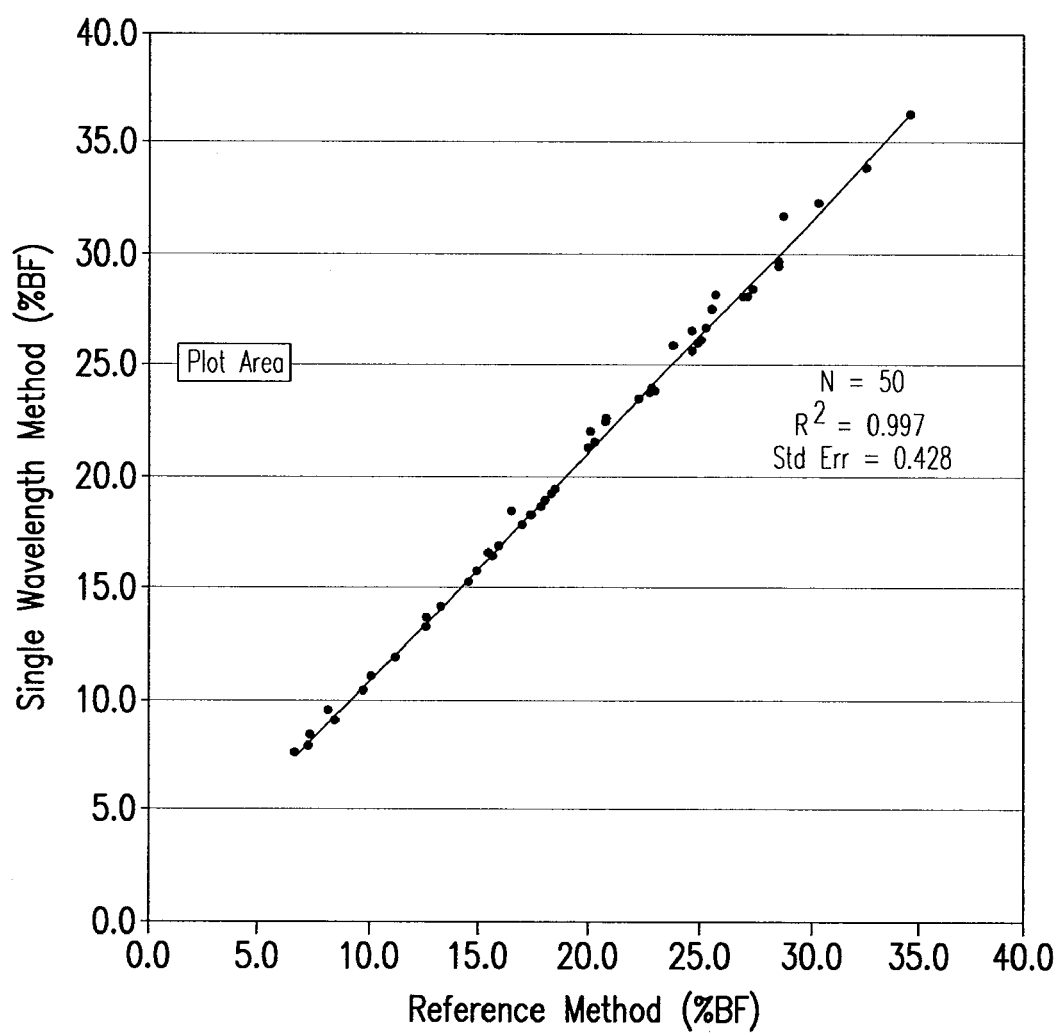
FIG. 5 is graph comparing the accuracy of a single wavelength body fat measurement approach to the accuracy of the FUTREX-6100 Professional Body Fat Analyzer.

FIG. 5 is a comparison of the accuracy of the single wavelength approach to the accuracy of the FUTREX-6100 Professional Body Fat Analyzer. As shown in the figure, there is a high correlation between the simple single wavelength approach to the more complex approach.

Figure 6:
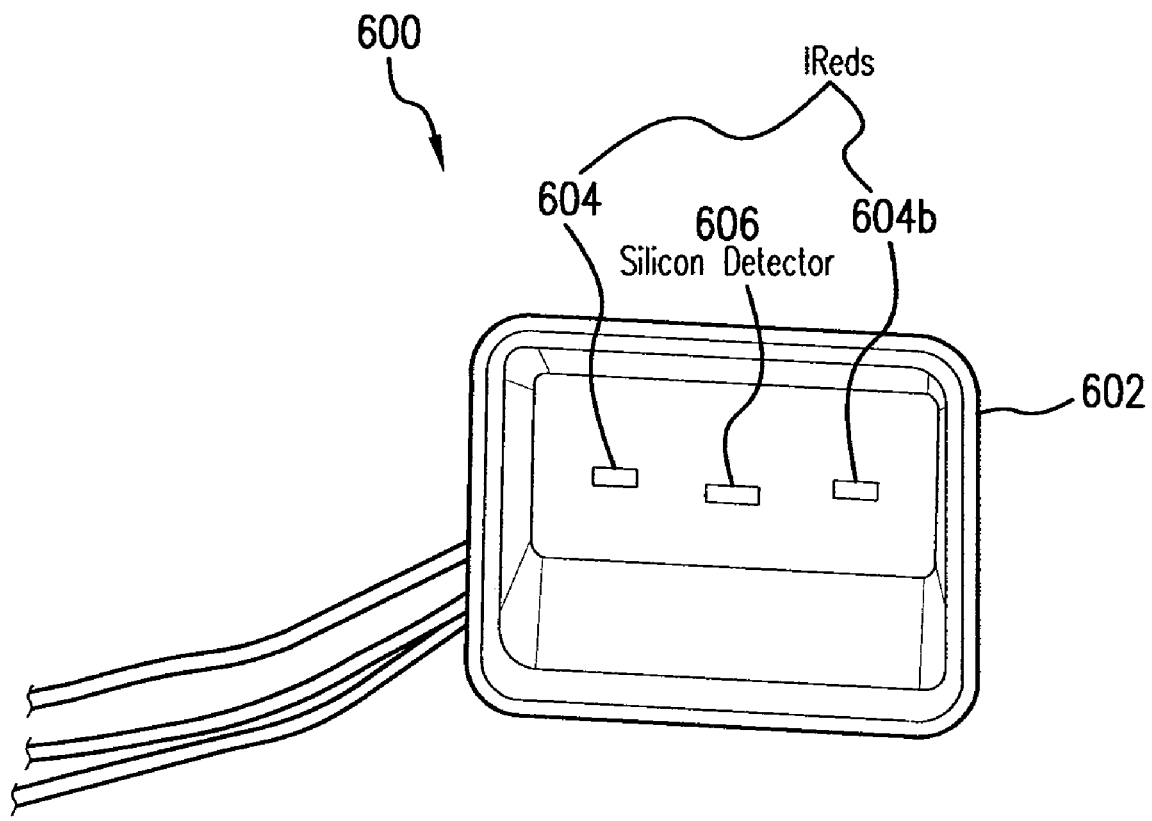
FIG. 6 illustrates a body fat measurement apparatus according to an embodiment.

Referring now to FIG. 6, FIG. 6 illustrates a body fat measurement apparatus 600 according to an embodiment of the invention. Apparatus 600 includes a housing 602 that houses one or more infrared emitting diodes (IREDs) 604. Preferably, each diode 604 emits infrared radiation having a wavelength of approximately 940 nanometers. Housing 602 also houses a detector 606 (e.g., a photodetector or other radiation detector). In the embodiment shown, apparatus 600 includes a first IRED 604a, a second IRED 604b and a detector 606 positioned midway between IRED 604a and IRED 604b. As shown, IREDs 604a,b and detector 606 may be aligned with each other. Housing 602 may also house a heater circuit 790 (see FIG. 7).

FIG. 6 illustrates the small size of the body fat measurement apparatus 600. The apparatus, after receiving external power, is self-contained and provides a linear output proportional to the light received at detector 606. The linear output is suitable for direct entry into an analog to digital converter that allows a microprocessor to combine the measured optical information with the subject's physical parameters, to determine percent body fat via a multiple linear regression equation.

Figure 7:
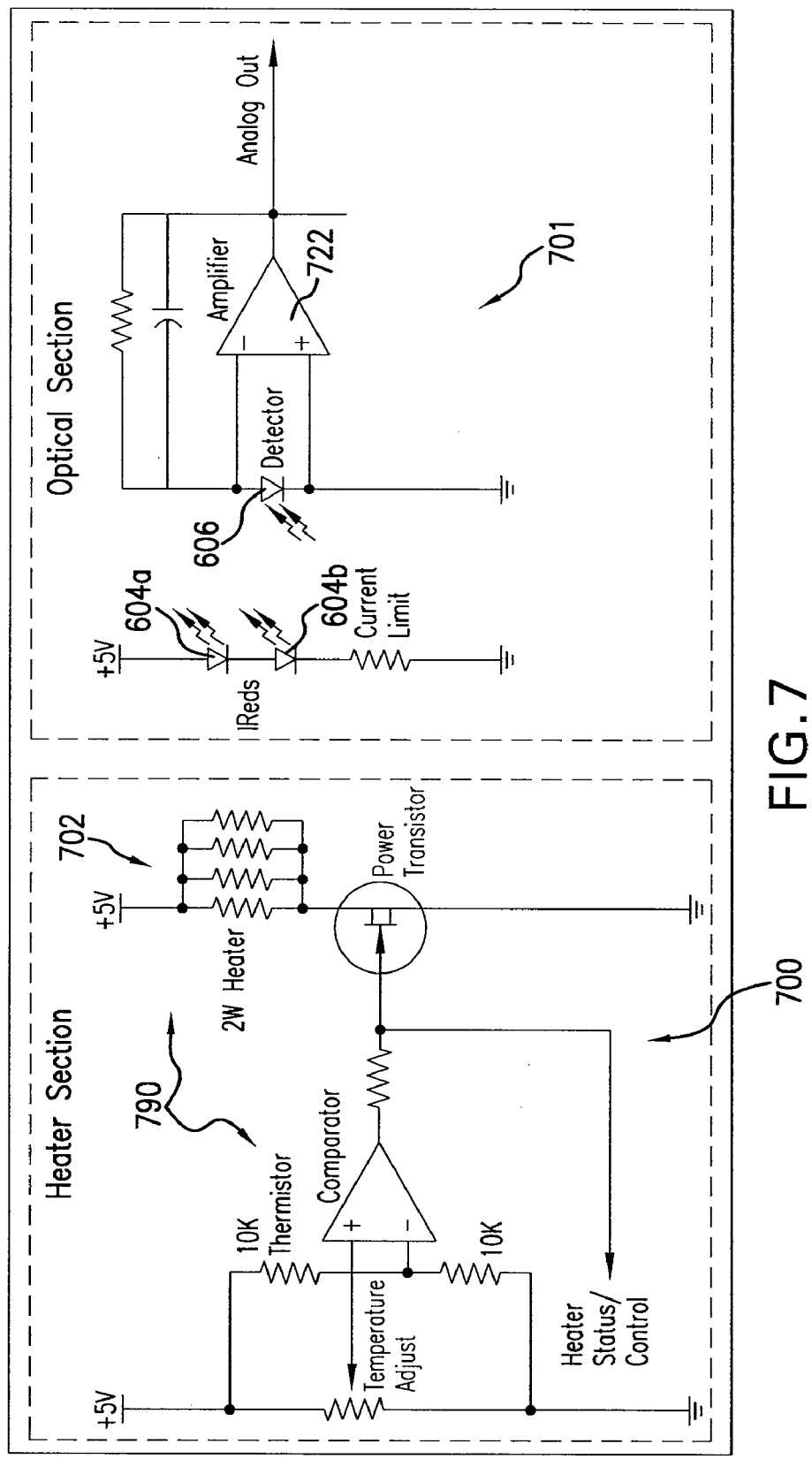
FIG. 7 illustrates a simplified circuit diagram of a body fat measurement apparatus according to an embodiment.

Referring now to FIG. 7, FIG. 7 is a simplified circuit diagram, according to one embodiment, of body fat measurement apparatus 600. As shown in the diagram and as described above, the optical section 701 of apparatus 600 may include two IREDs 604 and a silicon optical detector 606. Detector 606 may be coupled to an input of an amplifier 722.

The output of amplifier 722 may be input to a processing system (not shown) that may digitize the output to create digital data, store the digital data, and use the digital data to calculate body fat.

FIG. 7 also shows that apparatus 600 may include a heater section 700. Heater section 700 includes a heater circuit 790 that may include one or more resistor heaters 702 that control the temperature of apparatus 600 at approximately 35° C. (a tolerance of approximately +/−2° C.). This near constant temperature approach eliminates short-term drifts that are traditionally corrected for by "zeroing" the system with an optical standard after every measurement. Experiments have shown that by holding the body fat measurement apparatus 600 to a near constant temperature, zeroing with an optical standard does not need to be performed more than about once per month.

Figure 8:
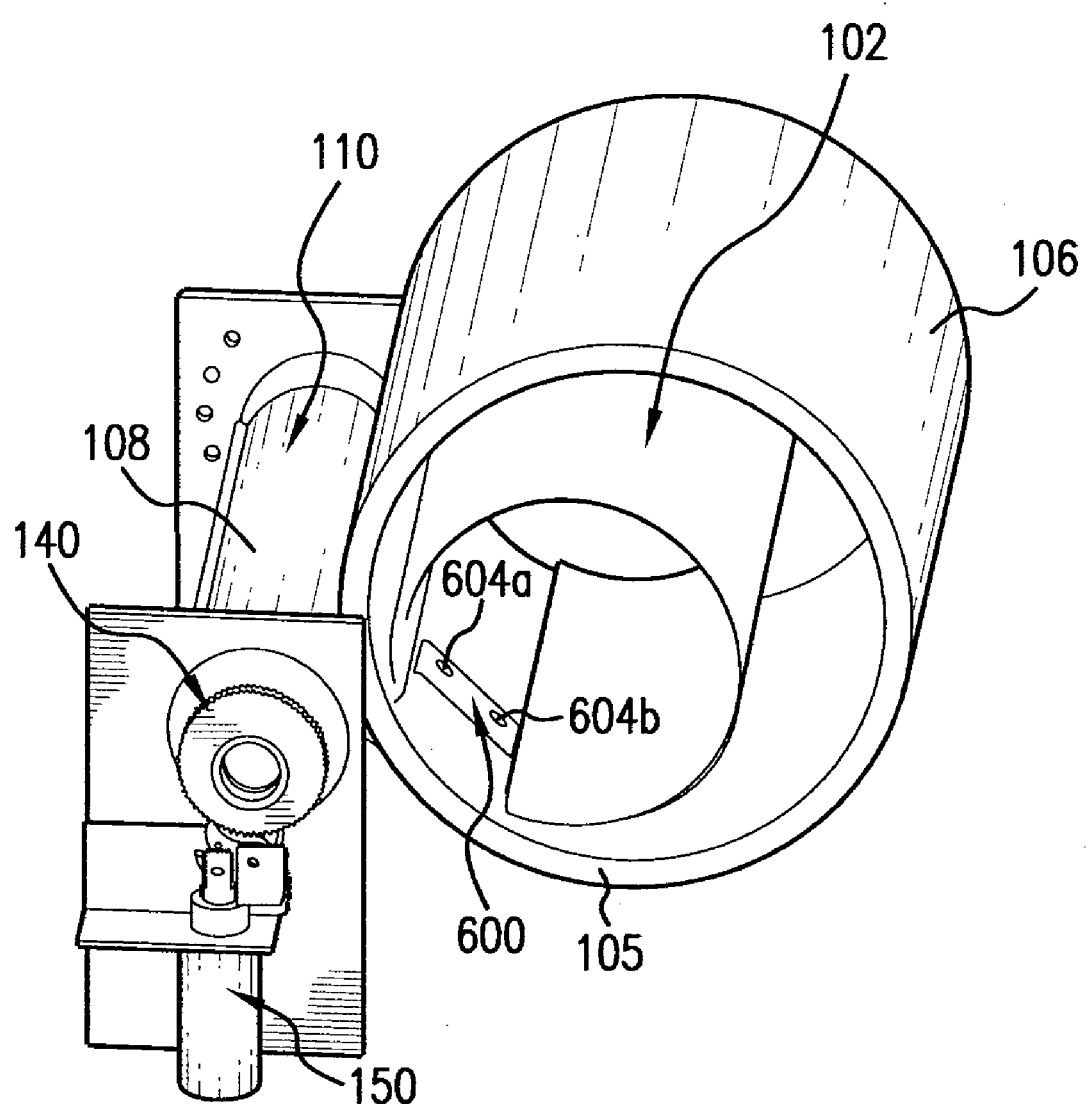
FIG. 8 illustrates a body fat measurement system integrated with a blood pressure measurement apparatus.

In preferred embodiments, body fat measurement apparatus 600 is combined with a blood pressure measurement apparatus, such as blood pressure measurement apparatus 100. This feature is illustrated in FIG. 8, which shows IREDs 604a and 604b protruding slightly from the inner wall of the support structure 106. So that IREDs 604a and 604b will be positioned in the triceps region, the IREDs are positioned adjacent to the proximal end 105 of support 106 (i.e., the end that is closest to the subject when the subject inserts his/her arm into cuff 102).

In some embodiments, during the period of time when the subject's blood pressure is being measured, the subject's body fat measurement is made. In some embodiments, the body fat measurement is made when the pressure on the subject's arm is approximately 10 to 20 mmHg.

The body fat measurement is preferably made via interactance where the optics is pressed against the arm during inflation of the blood pressure cuff, and thus, the light from the IRED(s) 604 enters the arm and then a fraction of the light is trans-reflected to detector 606. A simplistic explanation of this measurement concept is that people that are physically fit (i.e., are muscular), their arm is harder and it is difficult for light to go deep in the arm, and thus, the light trans-reflects close to the surface of the skin, and therefore, a high signal is achieved at the detector. For people that are less fit, their arms are "softer," thus light penetrates much further into the arm, and therefore, much less of a signal is returned to the detector.

Non-Invasive Fingertip Measurements

Figure 9:
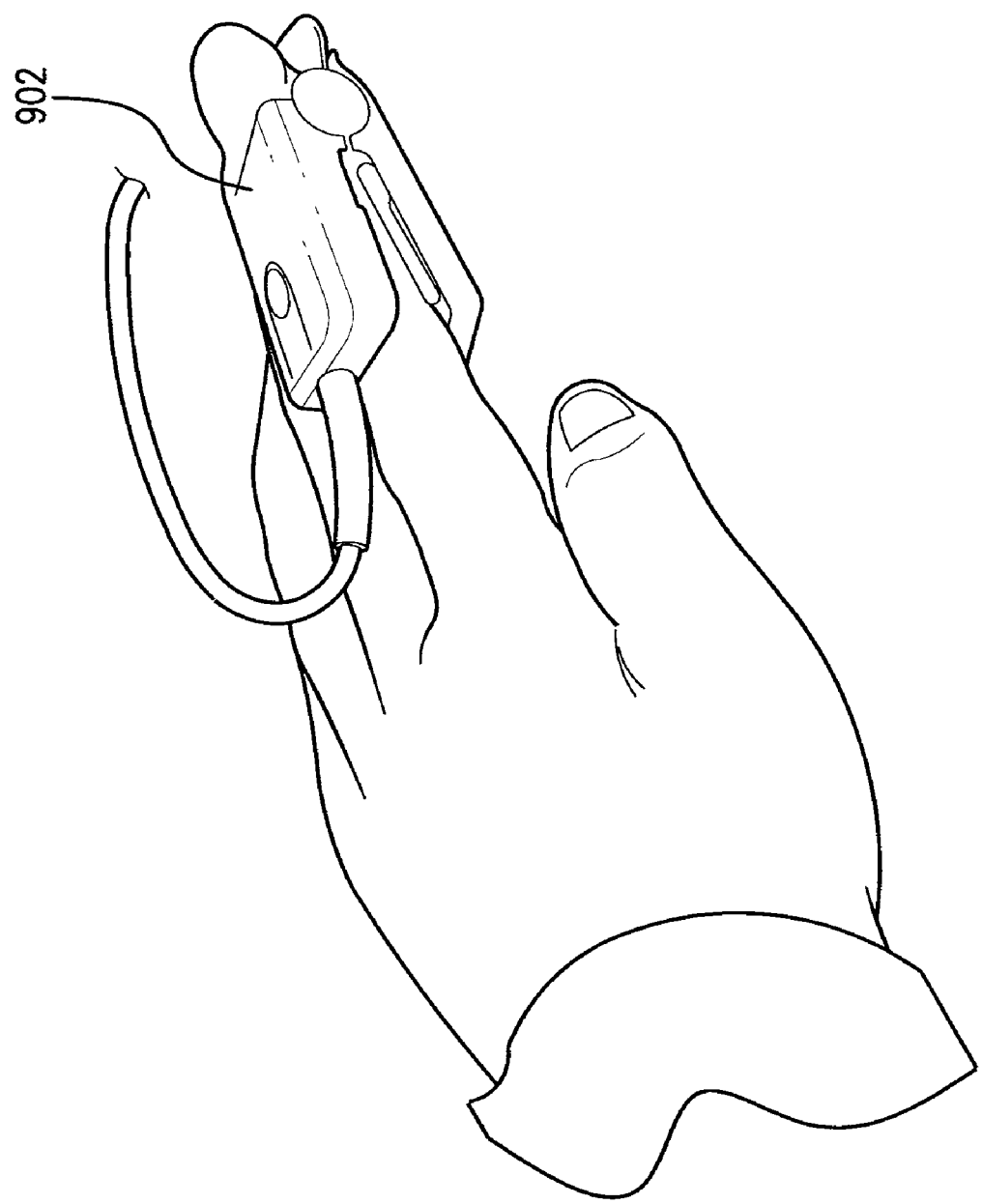
FIG. 9 shows a finger clip sensor.

In some embodiments, the invention provides a health kiosk apparatus that not only measures a subject's blood pressure and/or body fat, but also measures (1) the arterial oxygen saturation of haemoglobin (Hb), (2) blood analyte levels (e.g, blood gluclose, cholesterol, hemoglobin and other blood analytes), and (3) blood circulation. All of these measurements are performed at or about the same time the blood pressure and/or body fat measurements are being made using a pulse oximetry finger clip sensor 902 (see FIG. 9). Accordingly, in some embodiments, the present invention provides a self-service health kiosk that includes not only a cuff 102 and/or body fat measurement apparatus 600, but also a finger clip sensor 902 and a data processing apparatus (not shown) that includes a memory for storing data generated by finger clip sensor 902 and a processor for processing the data according to well known methods to determine the above described measurements.

Figure 10:
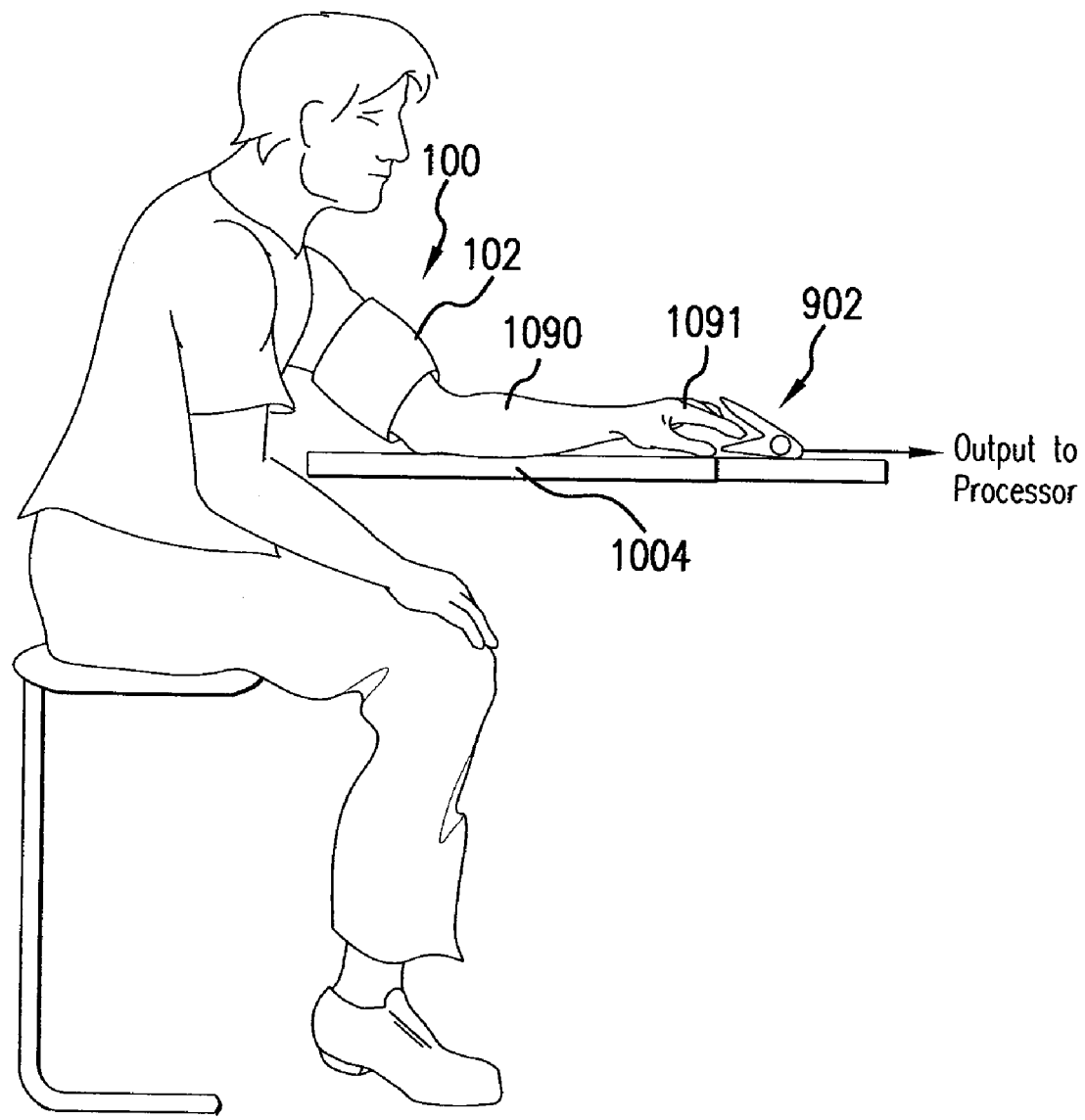
FIG. 10 illustrates a health kiosk according to an embodiment.

A blood pressure measurement kiosk allows the subject's forearm 1090 and hand 1091 of the arm inserted into the cuff 102 to lie essentially flat on a tabletop surface 1004 (see FIG. 10). This geometry allows finger clip type sensor 902 to be easily installed on a finger of the arm being measured. Such finger clip sensors 902 are common on pulse oximetry measurement systems.

Pulse oximetry finger clip sensor 902 provides two light transmission measurements; one at 910 to 940 nm, the other at 660 to 720 nm. The availability of transmission measurement data from the finger type sensor allows three different types of non-invasive measurements to be accomplished using a single fingertip sensor. These include: (1) the arterial oxygen saturation of haemoglobin (Hb) (Pulse Oximetry), (2) blood analyte levels (e.g, blood gluclose, cholesterol, hemoglobin and other blood analytes), and (3) blood circulation.

Pulse Oxymetry:

In pulse oxymetry, finger clip sensor 902 outputs two wavelengths of radiation that are transmitted through the finger tip of the finger inserted into finger clip sensor 902. By comparing change in light transmission of these two wavelengths during different portions of the heart pulsing cycle, the percent of oxygen saturation of hemoglobin in arterial blood (PSO2) can be determined. Such in-vivo measurement is common in almost all operating rooms and hospital recovery rooms. Such measurements are of particular interest to people that have previously had pneumonia or other lung or respiratory problems. Thus, PSO2 is a useful health related measurement to be available in a kiosk.

Blood Glucose and Other Blood Analyte Measurements:

U.S. Pat. Nos. 6,400,972 and 6,587,704, the contents of which are incorporated herein by this reference, teach that blood glucose, cholesterol, hemoglobin and other blood analytes may be determined using a pulse oximetry finger clip sensor 902. To perform the measurements of blood analytes requires analyzing the spectrum change that occurs at the two wavelength measurements between normal blood flow and when blood flow is occluded at the root of the finger.

Figure 11:
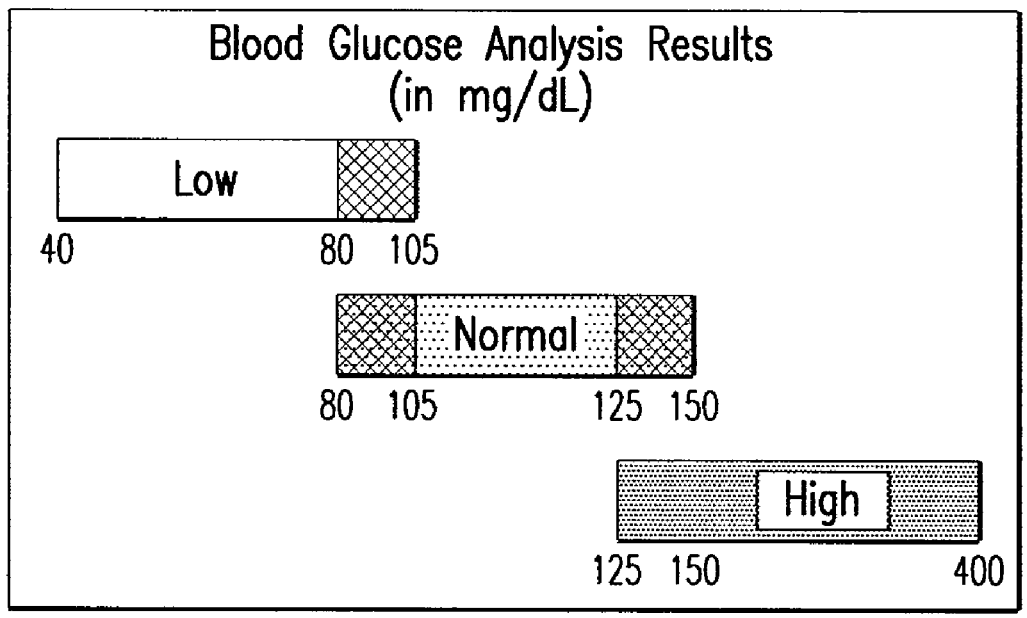
FIG. 11 illustrates information that may be outputted to a user of a health kiosk according to an embodiment.
Figure 11:
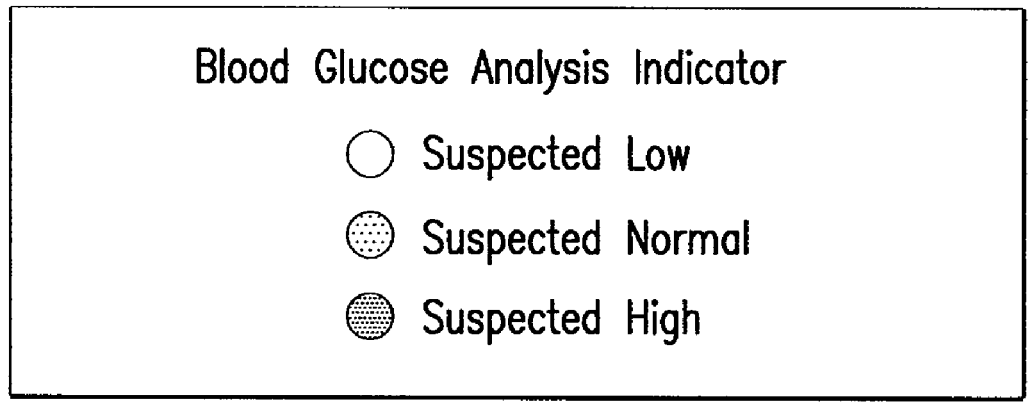

However, a blood pressure kiosk already includes an arm mounted cuff 102 that occludes the blood. Our research has demonstrated temporary cessation of blood flow in the arm also allows measurement of blood analytes, particularly blood glucose for people that have diabetes. However, the accuracy of such measurements is somewhat diminished. Fortunately, such kiosk provided measurements do not need to be to the accuracy of typical home blood glucose meters. It would suffice if the measurement simply provided three results that the blood glucose is either normal or low or high. This concept is illustrated in FIG. 11. Similar measurements can be provided for cholesterol and hemoglobin.

Blood Circulation Analysis:

The efficiency of blood circulation in the capillaries of the fingertip has been shown to be an early predictor of adult diseases such as cardiovascular including heart attack and strokes, certain types of cancer and others. This is described in the technical paper entitled "Acceleration Plethysmogram: A Method of Blood Circulation Analysis" by MISWA Institute of Research and Development, the content of which is incorporated herein by this reference.

The same technical paper describes a method of quantitative measurement of the status of blood circulation. In this method, trans-reflectance measurements are made at the fingertip using an IRED in the 920 to 940 region to obtain a pulse signal. The paper discloses quadratically differentiating the pulse signal to provide information or "indices" regarding the body's blood circulation.

We have discovered that a pulse signal can be obtained using light transmission measurements at the fingertip such as that provided by fingertip sensor 902. This pulse signal can also be quadratically differentiated to provide information or "indices" regarding the body's blood circulation. Thus, the same pulse oximetry sensor 902 that provides hemoglobin saturation in arterial blood and blood analytes (e.g., blood glucose) can also provide information regarding the blood circulation of the individual being tested.

In summary, fingertip sensor 902 enables all of the above described measurements to be performed during the time period that the blood pressure, pulse and body fat measurements are being made.

Accordingly, in some embodiments, the present invention provides a self-service health kiosk that includes not only a blood pressure measurement apparatus 100 and/or body fat measurement apparatus 600, but also a finger clip sensor 902 and a data processing apparatus (not shown) that includes a memory for storing data generated by finger clip sensor 902 and a processor for processing the data according to well known methods to determine the above described measurements.

Anti Oxident (Carotenoid) Determination

The scientific literature describes that carotenoid's content in the human body is inhibitors of a variety of cancer and pre-cancers including sustained remissions in oral Leukemia patients. It has also been shown in the literature that there is an inverse correlation between carotenoid level and age related macular degeneration, a leading cause of blindness ("Resonance Raman Detection of Carotenoid Antioxidants in Living Human Tissue"; Aug. 1, 2001/Vol. 26, No. 15/Optics Letters, the content of which is incorporated herein by this reference). The same scientific literature indicates that the site that is particularly well suited for accessing anti oxident levels in human skin is the inner palm. "This site is convenient, not only for accessibility, but also for the following reasons: (a) the carotenoid concentration in the palm are among the highest found on the skin (because carotenoids are lipophilic and palm skin has a high lipid/protein ratio), (b) differences in pigmentation among various skin types are minimal in the palm, and (c) the stratum corneum thickness of the palm (approximately 400 micrometers) is high compared to other skin sites."

Using this approach, Gellermann, et al. taught in U.S. Pat. No. 6,205,354, the content of which is incorporated herein by this reference, the technique of resonance Raman spectroscopy to measure levels of carotenoids.

We have discovered that similar measurements can be made using the much simpler approach of near-infrared quantitative spectroscopy. By installing into the a light probe (a.k.a., "light probe wand" or "light wand"), such as the light probes described in U.S. Pat. No. 6,134,458, the content of which is incorporated herein by this reference, a simple two-wavelength measurement, accurate determination of carotenoid level can be obtained using the light wand. These two wavelengths are approximately 488 nanometers and 520 nanometers. The simple palm measurement may be made during the same time as the fingertip measurements are made that are described above.

Figure 12:
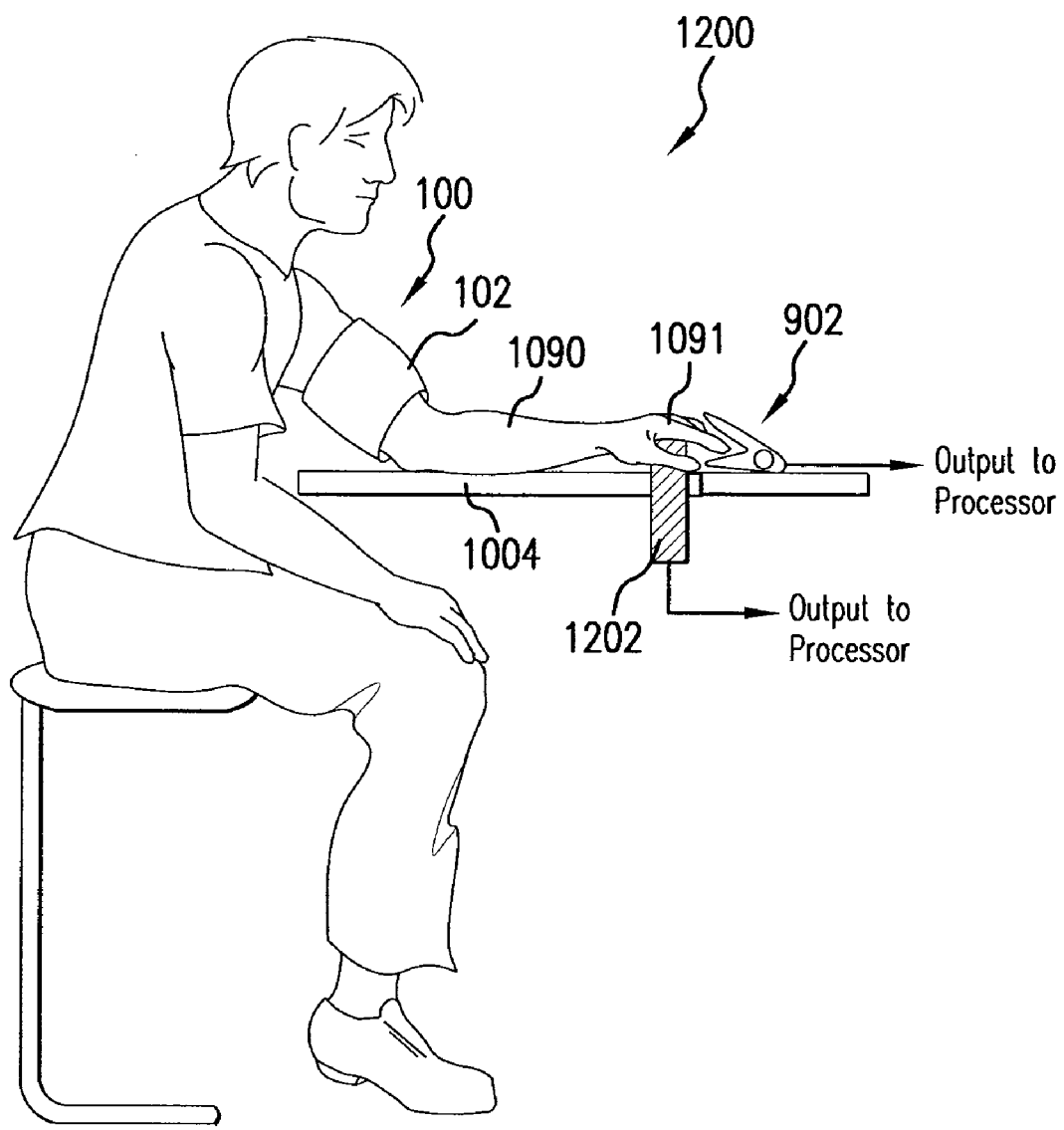
FIG. 12 shows a light probe incorporated into the self-service health kiosk.

Accordingly, in some embodiment, a light probe 1202 (see FIG. 12) as described above is incorporated into the self-service health kiosk 1200. The light probe 1202 is positioned so that the subject's palm rests on a surface of the light wand so that the radiation emitted by the light probe strikes the palm. Output from the detector(s) (not shown) of light probe 1202 are received by a processing unit (not shown) which uses the output to determine carotenoid level.

Wheelchair Accessibility

Figure 13:
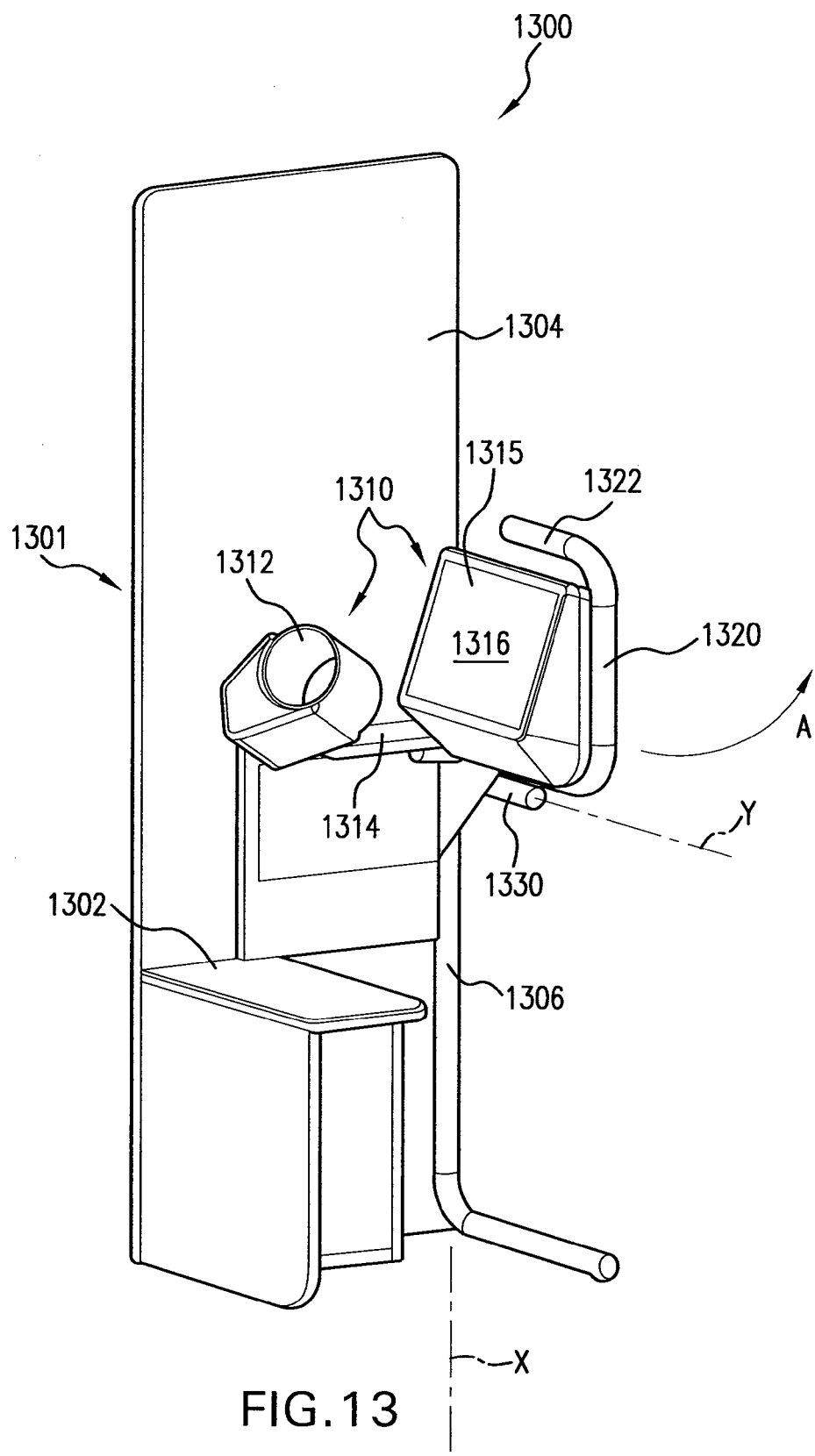
FIGS. 13-15 illustrate a wheelchair accessible health kiosk according to an embodiment.

FIG. 13 shows a wheel-char accessible self-service health kiosk 1300 according to an embodiment of the invention. As shown in FIG. 13, kiosk 1300 may include a seat 1302 (e.g., a bench seat or other seat) connected to support structure 1301 including a wall 1304 having a leg 1306 attached thereto. Leg 1306 may be implemented using a pipe or similar structure and may attach to wall 1304 at an edge thereof. Seat 1302 and leg 1306 may be placed on a floor of a retail establishment, such as on the floor of a drug-store.

Kiosk 1300 may also include a blood pressure measurement apparatus 1310 that is attached to a rigid support structure 1330, which support 1330 is pivotally connected to support 1301 such that support 1330, and hence apparatus 1310 which is connected thereto, may rotate generally about a longitudinal axis X of leg 1306, which is generally perpendicular to the floor on which support structure 1301 is placed. As shown in the figure, the longitudinal axis of support 1330 (see axis Y) is generally perpendicular to axis X. To facilitate rotation of apparatus 1310, an arm 1320 may be provided. Arm 1320 may be connected to support 1330 and may have a hand-grip portion 1322.

Blood pressure apparatus 1310 may include a blood pressure cuff 1312, a rigid, planar surface 1314, and a user interface system 1315, which may include a display 1316. Display 1316 may be a liquid crystal display (LCD) or other type of display for presenting information in visual form. Preferably, all of the components of apparatus 1310 are connected to support 1330. For example, cuff 1312 may be fixed to table 1314, which itself may be fixed to support 1330, thereby connecting cuff 1312 to support 1330. When a subject wishes to use blood pressure apparatus 1310 to obtain a blood pressure or other measurement, the subject may sit on seat 1302 facing display screen 1316 and insert his/her left arm through cuff 1312 such that the elbow and/or forearm of the left arm may rest on table 1314.

If a subject wishes to have apparatus 1310 make a measurement but the subject is unable to sit on seat 1302 (e.g., the subject is in a wheelchair), the subject, or an assistant, may rotate apparatus 1310 in a direction away from wall 1304. For example, by pushing on arm 1320, apparatus 1310 will rotate in the direction of arrow A.

Figure 14:
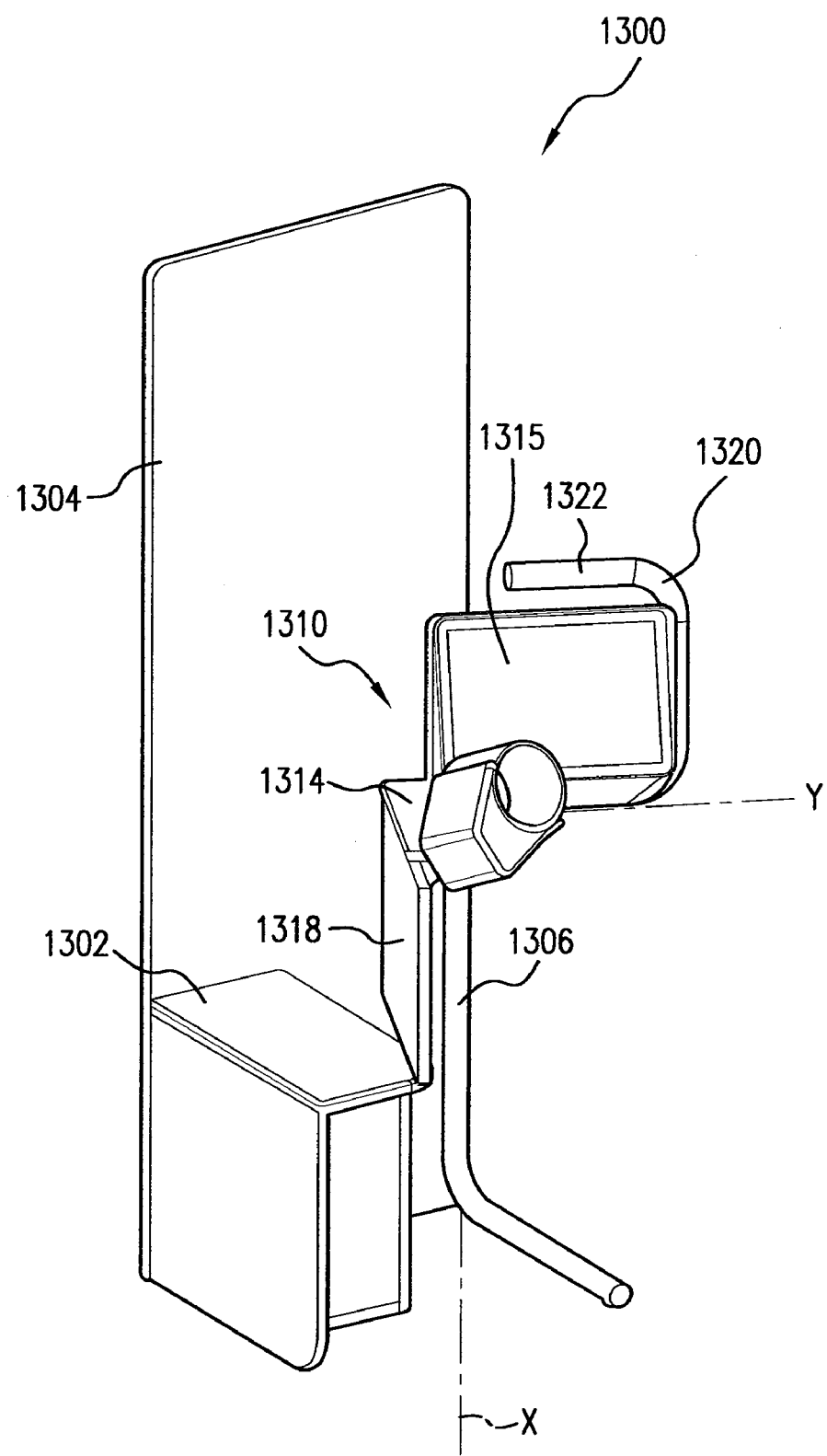
Figure 15:
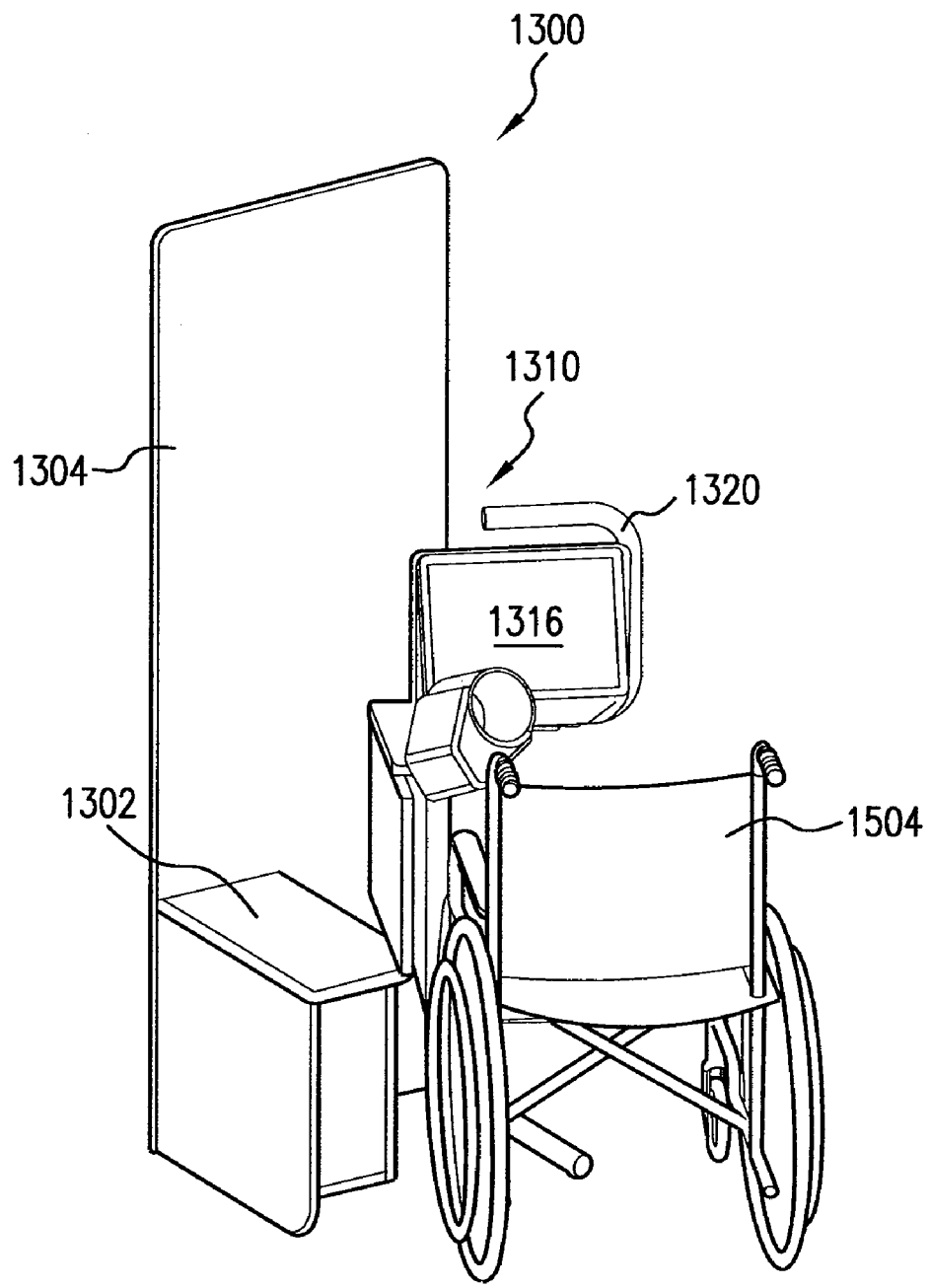

FIG. 14 shows kiosk 1300 after apparatus 1310 has been rotated away from wall 1304 by about 65 degrees. When apparatus is in the position shown in FIG. 14, kiosk 1300 is said to be in the "wheelchair measurement mode." Preferably, when kiosk 1300 is in the wheelchair measurement mode, a locking mechanism locks apparatus 1310 in place. As part of the rotation of apparatus 1310, a leg support 1318, which is connected to surface 1318, may move across the top of seat 1302 and comes to rest on the seat, thereby, providing stability for surface 1318. FIG. 15 shows that after apparatus 1310 has been positioned into wheelchair measurement mode, a wheelchair 1504 may be positioned in front of apparatus 1310 so that a subject in the wheelchair can use apparatus 1310. When the subject in the wheelchair is finished using apparatus 1310, the apparatus 1310 may be rotated back to its initial position as shown in FIG. 13.

As illustrated in FIGS. 13-15, when the apparatus 1310 is in the initial position (see FIG. 13), the opening of the cuff 1312 faces in the general direction of the seat so that the cuff is accessible to a subject sitting in the seat, and when the apparatus 1310 is in the wheelchair accessible position (see FIG. 15), the opening of the cuff 1312 does not face in the general direction of the seat so that the cuff 1312 is accessible to a person in a wheelchair.

Figure 16:
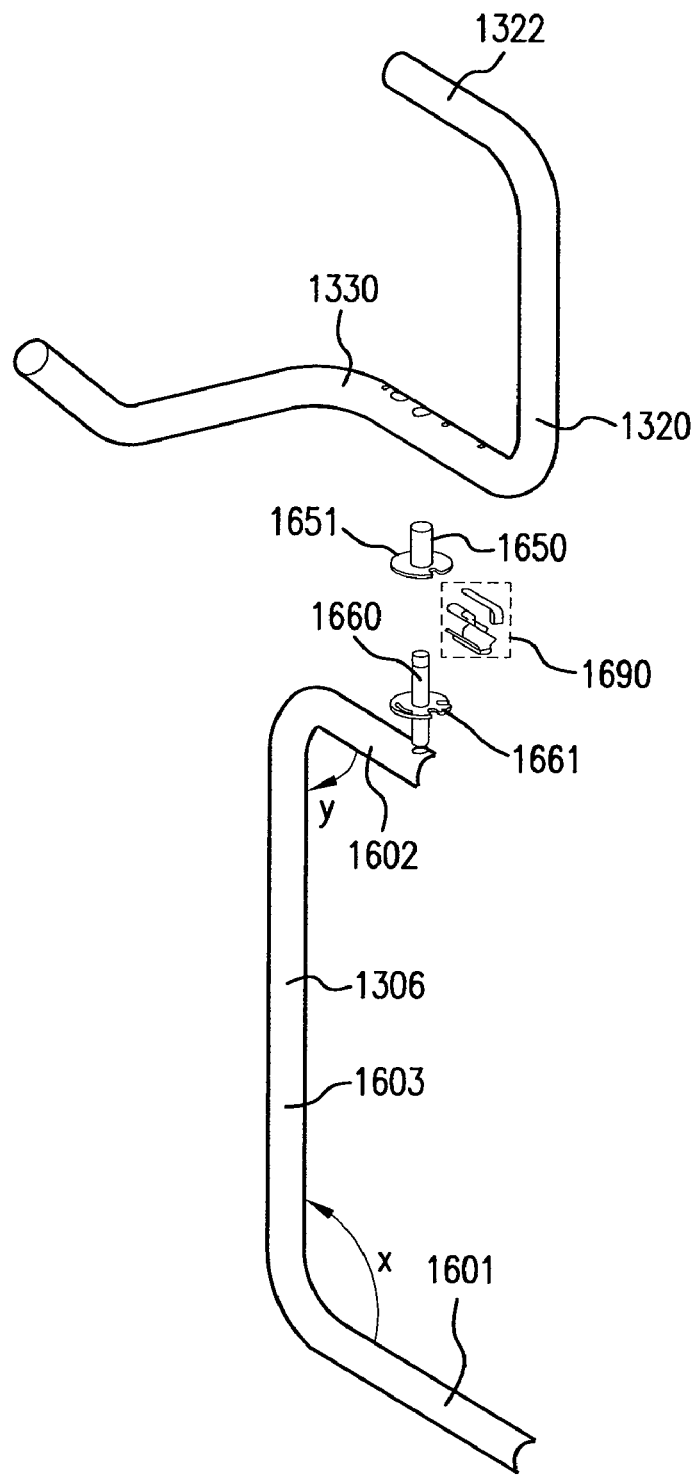
FIG. 16 illustrates a portion of a wheelchair accessible health kiosk according to an embodiment.

Referring now to FIG. 16, FIG. 16 illustrates a preferred embodiment of leg 1306 and support 1330. In the embodiment shown, leg 1306 consists of a first end section 1601 (a.k.a., "foot portion"), a second end section 1602 and an interim section 1603 between the end sections. The end sections 1601 and 1602 are angled with respect to the interim section 1603. An angle x formed between the end section 1601 and interim section 1603 is preferably about 90 degrees. Similarly, an angle y formed between the end section 1602 and interim section 1603 is also preferably about 90 degrees. Thus, in one embodiment, end section 1601 is generally parallel and spaced apart from end section 1602.

In one embodiment, as shown in FIG. 16, support 1330 pivotally attaches to end section 1602 of leg 1306. For example, a rod or tube 1660 (hereafter "rod 1660") may be used to pivotally join support 1330 to leg 1306. In the example shown, a washer 1661 is placed on rod 1660 and is disposed a distance away from each end of rod 1660. One end of rod 1660 inserts into a hole in a top surface of end section 1602 and the opposite end of rod 1660 inserts into an end of a tube 1650. The opposite end of tube 1650 is inserted into a hole on a bottom surface of support 1330. A washer 1651 may be placed on the end of tube 1650 into which rod 1660 is inserted. This arrangement of parts allows support 1330 to move only rotationally with respect to leg 1306. More specifically, support 1330 may rotate around the longitudinal axis of rod 1660, which axis is preferably generally perpendicular with a surface (e.g., a floor) on which end section 1601 rests.

As further shown in FIG. 16, a latch release system 1690 may be provided. Latch release system 1690 functions to enable and disable the rotational movement of support 1330 with respect to leg 1306.

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A blood pressure and body fat measurement method, comprising:
   (1) using a blood pressure measurement apparatus, said blood pressure measurement apparatus comprising:
      a tubular or semi-tubular support member having an inner surface and an outer surface; and
      an inflatable cuff for receiving a subject's arm; and
   (2) using a body fat analyzer, said body fat analyzer comprising:
      a first infrared emitting diode for emitting infrared radiation having a single wavelength;
      a second infrared emitting diode for emitting infrared radiation having a single wavelength that is the same as the wavelength of the radiation emitted by the first infrared emitting diode; and
      a detector positioned midway or about midway between the first and second diodes, wherein
      said body fat analyzer is disposed such that when a subject places an arm fully into the inflatable cuff, the diodes are disposed next to a triceps region of the arm, said step of using the body fat analyzer comprises inserting an arm into the cuff in such a way that the diodes are disposed next to a triceps region of the arm, and
      said body fat analyzer measures body fat using only the single wavelength.

2. The method of claim 1, wherein said cuff has a first end and a tail portion, the first end being fixed to the inner surface of the support member and the tail portion passing through a slit in the support member and being at least partially wound around a roller, said cuff comprising a casing housing an inflatable bladder and a hard yet flexible frame.

3. The method of claim 2, wherein said frame is generally planar when not flexed.

4. The method of claim 2, further comprising a ratchet wheel attached to one end of said roller.

5. The method of claim 4, further comprising a ratchet and pawl configured to lock said gear when the apparatus is in a measurement mode so that said roller can not rotate while the apparatus is in the measurement mode.

6. The method of claim 5, wherein said bladder is configured to inflate in response to the apparatus being placed in the measurement mode.

7. The method of claim 5, wherein the apparatus is placed in the measurement mode in response to activation of a start measurement button.

8. A blood pressure and body fat measurement method, comprising:
   obtaining a blood pressure measurement apparatus, said blood pressure measurement apparatus comprising an inflatable cuff for receiving a subject's arm; and
   obtaining a body fat analyzer, said body fat analyzer comprising:
      a first infrared emitting diode for emitting infrared radiation having a single wavelength;
      a second infrared emitting diode for emitting infrared radiation having a single wavelength that is the same as the wavelength of the radiation emitted by the first infrared emitting diode; and
      a detector positioned midway or about midway between the first and second diodes, wherein
      said body fat analyzer is disposed such that when a subject places an arm fully into the inflatable cuff, the diodes are disposed next to a triceps region of the arm; and
   instructing a user to place an arm into the inflatable cuff in such an orientation that the diodes are disposed next to a triceps region of the arm, wherein
   said body fat analyzer is configured to measure body fat using only the single wavelength.

9. The method of claim 8, wherein the inflatable cuff comprises a casing and a flexible, resilient frame and an inflatable bladder housed within the casing.

10. The method of claim 8, wherein the blood pressure measurement apparatus further comprises a roller and the tail portion is wrapped around the roller.

11. The method of claim 8, wherein the support member is tubular or semi-tubular in shape.

12. The method of claim 8, wherein said single wavelength is about 940 nanometers.

13. The method of claim 8, wherein said body fat analyzer further comprises a heating circuit.

14. The method of claim 13, wherein said body fat analyzer further comprises (a) a housing, wherein said diodes, said detector and said heating circuit are housed in said housing, and (b) an amplifier for amplifying a signal produced by said detector, said amplifier also being housed in said housing.

* * * * *